(12) United States Patent
Biber (10) Patent No.: US 9,322,891 B2
(45) Date of Patent: Apr. 26, 2016

(54) LOCAL COIL WITH A NUMBER OF SEPARATELY SWITCHABLE LOCAL COIL SHIM COILS

(75) Inventor: Stephan Biber, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 848 days.

(21) Appl. No.: 13/564,638

(22) Filed: Aug. 1, 2012

(65) Prior Publication Data
US 2013/0193968 A1   Aug. 1, 2013

(30) Foreign Application Priority Data

Aug. 2, 2011   (DE) .......................... 10 2011 080 275

(51) Int. Cl.
| | |
|---|---|
| *G01R 33/387* | (2006.01) |
| *G01R 33/341* | (2006.01) |
| *G01R 33/565* | (2006.01) |
| *A61B 5/055* | (2006.01) |
| *G01R 33/44* | (2006.01) |
| *A61B 5/00* | (2006.01) |

(52) U.S. Cl.
CPC .............. *G01R 33/387* (2013.01); *A61B 5/055* (2013.01); *G01R 33/341* (2013.01); *G01R 33/44* (2013.01); *G01R 33/5659* (2013.01); *A61B 5/6822* (2013.01)

(58) Field of Classification Search
CPC .... G01R 33/44; G01R 33/341; G01R 33/387; G01R 33/5659; A61B 5/055; A61B 5/6822
See application file for complete search history.

(56) References Cited

U.S. PATENT DOCUMENTS

| | | | | |
|---|---|---|---|---|
| 4,994,935 | A * | 2/1991 | Takechi | 361/141 |
| 5,250,902 | A * | 10/1993 | Williams et al. | 324/320 |
| 5,359,289 | A * | 10/1994 | van der Meulen | 324/320 |
| 5,650,724 | A | 7/1997 | Yamagata | |
| 6,014,069 | A * | 1/2000 | Havens et al. | 335/216 |
| 6,023,167 | A | 2/2000 | DeMeester et al. | |
| 6,100,695 | A * | 8/2000 | DeMeester et al. | 324/318 |
| 6,265,960 | B1 * | 7/2001 | Schauwecker et al. | 335/301 |
| 6,816,046 | B1 * | 11/2004 | Varney | 335/216 |
| 6,943,551 | B2 | 9/2005 | Eberler et al. | |
| 7,199,585 | B2 * | 4/2007 | Kruiskamp et al. | 324/320 |
| 8,013,607 | B2 * | 9/2011 | DeMeester et al. | 324/318 |
| 2012/0323113 | A1 | 12/2012 | Biber | |

FOREIGN PATENT DOCUMENTS

| | | |
|---|---|---|
| DE | 103 14 215 B4 | 11/2006 |
| DE | 10 2011 077 724 A1 | 12/2012 |

OTHER PUBLICATIONS

German Office Action dated May 15, 2012 for corresponding German Patent Application No. DE 10 2011 080 275.4 with English translation.

(Continued)

*Primary Examiner* — Dixomara Vargas
(74) *Attorney, Agent, or Firm* — Lempia Summerfield Katz LLC (57) ABSTRACT

A local coil for an imaging system includes a number of shim coils. A current for generating a shim field in one of the shim coils may be switched on and switched off. A current for generating a shim field in another of the shim coils may be switched on and switched off. The currents may be switched on and switched off independently of one another for generating a respective shim field in the shim coils.

42 Claims, 6 Drawing Sheets

(56) References Cited

OTHER PUBLICATIONS

C. Juchem et al., "Magnetic Field Homogenization of the Human Prefrontal Cortex With a Set of Localized Electrical Coils," Magnetic Resonance in Medicine 63, pp. 171-180, 2010.

J. Hsu et al., "Mitigation of Susceptibility-Induced Signal Loss in Neuroimaging Using Localized Shim Coils," Magnetic Resonance in Medicine 53, pp. 243-248, 2005.

J. Wilson et al., "Utilization of an Intra-Oral Diamagnetic Passive Shim in Functional MRI of the Inferior Frontal Cortex," Magnetic Resonance in Medicine 50, pp. 1089-1094, 2003.

R. Cusack et al., "An evaluation of the use of passive shimming to improve frontal sensitivity in fMRI," NeuroImage 24, pp. 82-91, 2005.

German Office Action dated Jan. 21, 2013 for corresponding German Patent Application No. DE 10 2011 080 275.4 with English translation.

* cited by examiner

LOCAL COIL WITH A NUMBER OF SEPARATELY SWITCHABLE LOCAL COIL SHIM COILS

This application claims the benefit of DE 10 2011 080 275.4, filed on Aug. 2, 2011.

BACKGROUND

The present embodiments relate to a method and a local coil for an imaging system.

Magnetic resonance tomographs (MRTs) (e.g., for examination of patients by magnetic resonance tomography) are known from DE10314215B4, for example.

Shims are described in:
1. Christoph Juchem, et al., "Magnetic field homogenization of the human prefrontal cortex with a set of localized electrical coils," Journal of Magnetic Resonance Imaging, MRM, 63: 171-180, 2010;
2. G H Glover et al., "Mitigation of susceptibility-induced signal loss in neuroimaging using localized shim coils," MRM 2005, 243-248;
3. R. Cusack et al., "An evaluation of the use of passive shimming to improve frontal sensitivity in fMRI," Neuroimage," 2005; 24, 82-91; and
4. J L Wilson et al., "Utilization of an intra-oral diamagnetic passive shim in functional MRI of the inferior frontal cortex," MRM 2003, 50, 1089-1094.

SUMMARY AND DESCRIPTION

The present embodiments may obviate one or more of the drawbacks or limitations in the related art. For example, the imaging of an imaging system may be efficiently optimized.

In one embodiment, adaptive shim coils within local coils, which may also function with existing coil interfaces, are provided.

As well as specific geometries for implementing the shim coil, a dynamic shim method that deals with power dissipation in an economical manner is provided. The shim is only applied during the TX pulse.

DETAILED DESCRIPTION OF THE DRAWINGS

Figure 11:
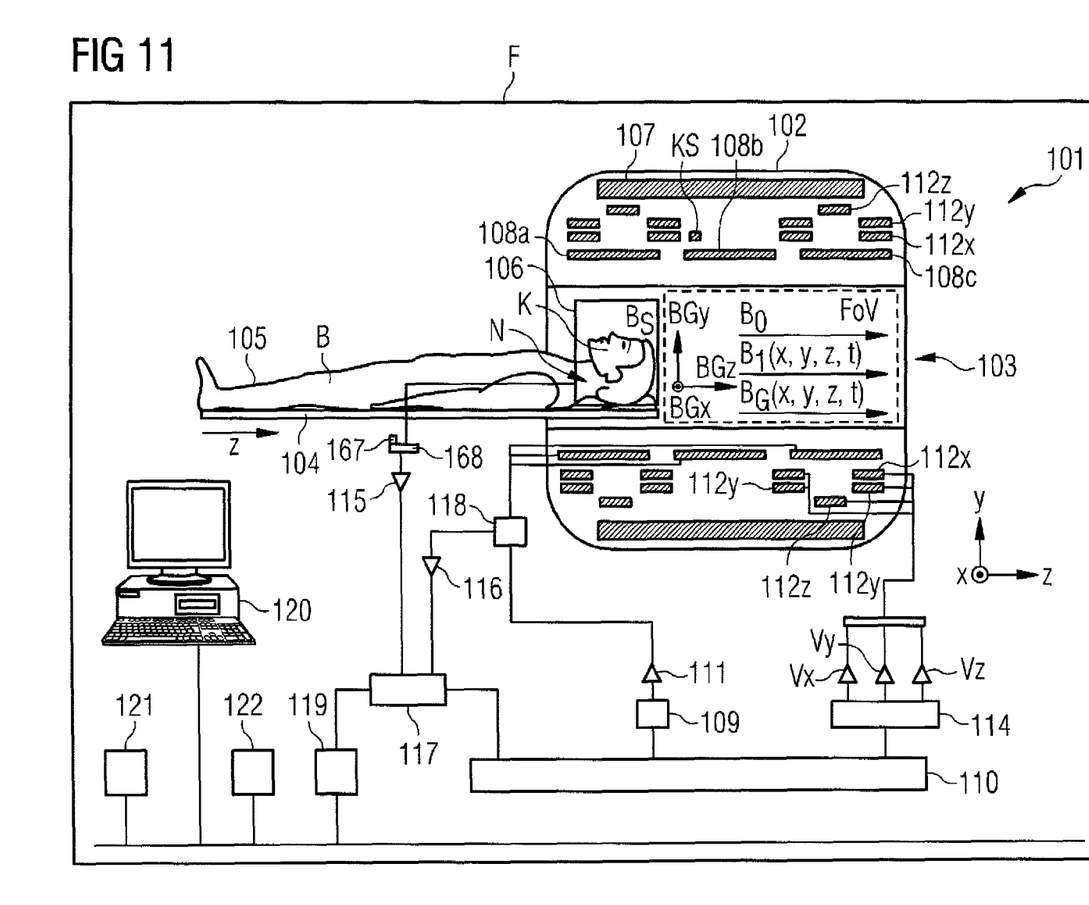
FIG. 11 shows a schematic of one embodiment of a magnetic resonance tomography (MRT) system.

FIG. 11 shows an imaging magnetic resonance device MRT 101 (e.g., a magnetic resonance tomograph; located in a shielded room or Faraday cage F) with a whole-body coil 102 having a space 103 (e.g., a tubular space), into which a patient couch 104 with a body 105 (e.g., of an object under examination such as a patient; with or without a local coil arrangement 106) may be moved in the direction of the arrow z in order to generate images of the patient 105 through an imaging method. Disposed on the patient 105, for example, is the local coil arrangement 106, with which, in a local area (e.g., a field of view (FOV)) of the MRT 101, images of a part area of the body 105 in the FOV may be generated. Signals of the local coil arrangement 106 may be evaluated by an evaluation device (e.g., including elements 168, 115, 117, 119, 120, 121) of the MRT 101 able to be connected, for example, via coaxial cable or wirelessly (e.g., element 167) to the local coil arrangement 106 (e.g., converted into pictures, stored or displayed).

In order to examine the body 105 (e.g., an object to be examined or a patient) using magnetic resonance imaging with the magnetic resonance tomograph MRT 101, different magnetic fields attuned to one another as precisely as possible in temporal and spatial characteristics are beamed (e.g., radiated) onto the body 105. A strong magnet (e.g., a cryomagnet 107) in a measurement chamber with a tunnel-shaped opening, for example, generates a statically strong main magnetic field $B_0$, that amounts, for example, to 0.2 Tesla to 3 Tesla. The body to be examined 105 is supported on a patient couch 104 and is moved into a roughly homogeneous area of the main magnetic field $B_0$. The nuclear spin of atomic nuclei of the body 105 is excited magnetically via high-frequency excitation pulses B1(x, y, z, t) that are beamed in via an antenna shown in a simplified form, for example, as a body coil 108 (e.g., a multipart body coil 108a, 108b, 108c; and/or if necessary, a local coil arrangement). High-frequency excitation pulses are generated, for example, by a pulse generation unit 109 that is controlled by a pulse sequence control unit. After amplification by a high-frequency amplifier 111, the high-frequency excitation pulses are conveyed to the high-frequency antenna. The high-frequency system shown in FIG. 11 is indicated schematically. In other embodiments, more than one pulse generation unit 109, more than one high-frequency amplifier 111 and a number of high-frequency antennas 108a, b, c are used in one magnetic resonance tomograph 101.

The magnetic resonance tomograph 101 also includes gradient coils 112x, 112y, 112z, with which magnetic gradient fields are beamed in during a measurement for selective slice excitation and for local encoding of the measurement signal. The gradient coils 112x, 112y, 112z are controlled by a gradient coil control unit 114 that, like the pulse generation unit 109, is connected to the pulse sequence control unit 110.

Signals sent out by the excited nuclear spin (e.g., of the atomic nuclei in the object under examination) are received by the body coil 108 and/or at least one local coil arrangement 106, amplified by assigned high-frequency preamplifiers 116 and further processed and digitized by a receive unit 117. The recorded measurement data is digitized and held as complex numerical values in a k-space matrix. An associated MR image may be reconstructed from the k-space matrix occupied by values using a multidimensional Fourier transformation.

For a coil that may be operated both in transmit and also in receive mode (e.g., the body coil 108 or the local coil 106), the correct signal forwarding is regulated by an upstream transmit-receive switch 118.

An image processing unit 119 generates, from the measurement data, an image that may be presented via an operating console 120 to a user and/or stored in a memory unit 121. A central processing unit controls the individual system components.

In MR tomography, images with a high signal-to-noise ratio (SNR) may be recorded with local coil arrangements (e.g., coils, local coils). These are antenna systems that are attached in the immediate vicinity on (e.g., anterior), below (e.g., posterior), on, or in the body 105. During an MR measurement, the excited nuclei induce a voltage in the individual antennas of the local coil. The induced voltage is amplified by a low-noise preamplifier (e.g., LNA, preamp) and is forwarded to the receive electronics. To improve the signal-to-noise ratio, even with high-resolution images, high-field systems (e.g., 1.5 T-12 T or more) are used. If more individual antennas are able to be connected to an MR system than there are receivers available, a switching matrix (e.g., an RCCS) is installed, for example, between receive antennas and receivers. This routes the currently active receive channels (e.g., the receive channels that lie right in the field of view of the magnet/MRT) onto the available receivers. This makes it possible to connect more coil elements than there are receivers present, since for whole body coverage, only the coils that are located in the FoV and/or in the homogeneity volume of the magnet of the MRT are to be read out.

Local coil arrangement 106 may, for example, be an antenna system that may, for example, include one or more antenna elements (e.g., coil elements). The individual antenna elements are, for example, embodied as loop antennas (e.g., loops) or butterfly coils, flexible coils or saddle coils. A local coil arrangement includes coil elements, a preamplifier, further electronics (e.g., sheath wave filters) and cabling, a housing and may include a cable with a plug connector, through which the local coil arrangement is connected to the MRT system. A receiver 168 accommodated on the system side filters and digitizes signals received from the local coil 106 and transfers generated data based thereon to a digital signal processor. The digital signal processor may derive an image or a spectrum from the measurement and make the image or the spectrum available to the user for subsequent diagnosis and/or storage.

FIGS. 1-10 show examples of exemplary embodiments of local coils 106 with one or more local coils.

In MR tomography, images with a high signal-to-noise ratio (SNR) may be recorded with local coil arrangements. These are antenna systems that are attached in the immediate vicinity on (e.g., anterior), below (e.g., posterior), on, or in the body 105. During an MRT measurement, the excited nuclei induce a voltage in the individual antennas of the local coil. The induced voltage is amplified with a low-noise preamplifier (e.g., LNA, Preamp) and forwarded to the receive electronics. To improve the signal-to-noise ratio, even with high-resolution images, high field systems are used (e.g., 1.5 T to 12 T and more)

The homogeneity of the $B_0$ basic field is of importance in many clinical MRT applications. During deviations of the homogeneity, artifacts or distortions may occur, or specific applications such as FatSat no longer function. FatSat is a technique, in which the frequency displacement of the protons bound in fat is used in order, through a high send pulse (e.g., saturation pulse) at the fat frequency, to filter out the signals from fatty tissue. The difference between the proton frequency in water and fat is small (e.g., a few ppm of the basic field), and this technique depends on the spatial homogeneity of the basic field. This may already be achieved over volumes of approximately 30×30×30 cm with up to 0.5 ppm.

For example, in the nape of the neck region, because of the spatially inhomogeneous distribution of the susceptibility (mu_r) of the body tissue, distortions of the $B_0$ basic field arise. Some of these may be corrected with shim coils built into the MRT system.

One problem in the use of such coils is a less than optimum fat saturation, for example. Fatty tissue, for example, in the nape of the neck area still appears bright in the image, although a fat saturation is designed to hide the fatty tissue. The reason for this may be that, because of the local $B_0$ variation, the fatty tissue does not have the expected resonant frequency. The saturation pulse that is intended to fully remove the spin of the fatty tissue does not reach this spin, since the reference frequency lies elsewhere.

The present embodiments efficiently provide a technical implementation on existing MR devices (e.g., there is no extra power supply on such devices for shim coils within local coils).

The present embodiments allow a specific definition of the shim field with respect to the spatial structure and strength, for example.

To keep the current induced by the gradient system parts as small as possible, in addition to the decoupling of the gradient system, current limiting by insertion of a resistor may be advantageous.

Since no interfaces are available at local coil interfaces on current MR scanners from large manufacturers that allow the current through the shim coil and thus the strength of the magnetic field generated by the coil to be varied (e.g., like the power supply of a conventional shim coil can), a number of coils, the fields of which may overlay each other constructively or destructively, may be used. Since the shim field is then composed of the sum of the fields of different coils, the use of a number of coils with an appreciable spatial distance of the leads from one another also gives the opportunity of not only varying the strength of the shim field but also the structure. This is helpful for adaptation of the field to different patients. Shown in FIGS. 1-10 are a number of possible embodiments of shim coils for the nape of the neck area. In these embodiments, the geometrical shape also plays a role.

Available at coil interfaces are primary supply voltage for coil electronics (e.g., 3-10V) and switchover signals for pin diodes. The switchover signals may switch between two states, a negative and a positive voltage. The switchover may be from −30V voltage to +100 mA current. In one embodiment, an intermediate state with +10 mA current may be used. The use of current sources for the pin diodes may be used as a shim coil power source. The tolerances are acceptable for use as a shim coil power source (e.g., <10%) when the voltage source (e.g., −30V) is used as a power supply for the shim coil.

To reduce the power demand and the heat dissipation, the LC shim may only be operated during the transmit phase of the MR system. For FatSat methods based on chemical shift, this may be sufficient. Thus, in addition to the circuit technology and architectural configuration, a method that only applies the local shim currents during the saturation pulse is also provided.

As well as decoupling from the gradient system by separate decoupling coils (e.g., up to three coils, one for each spatial direction, orthogonal to one another), a reduction of the gradient-induced currents may also be provided by series connection of a resistor (e.g., 5-500 Ohm).

The power consumption in this resistor may only be greatly reduced by application of the shim current during the transmit phase as mentioned above (e.g., according to the duty ratio TX/RX (factor 10-100)).

Figure 1:
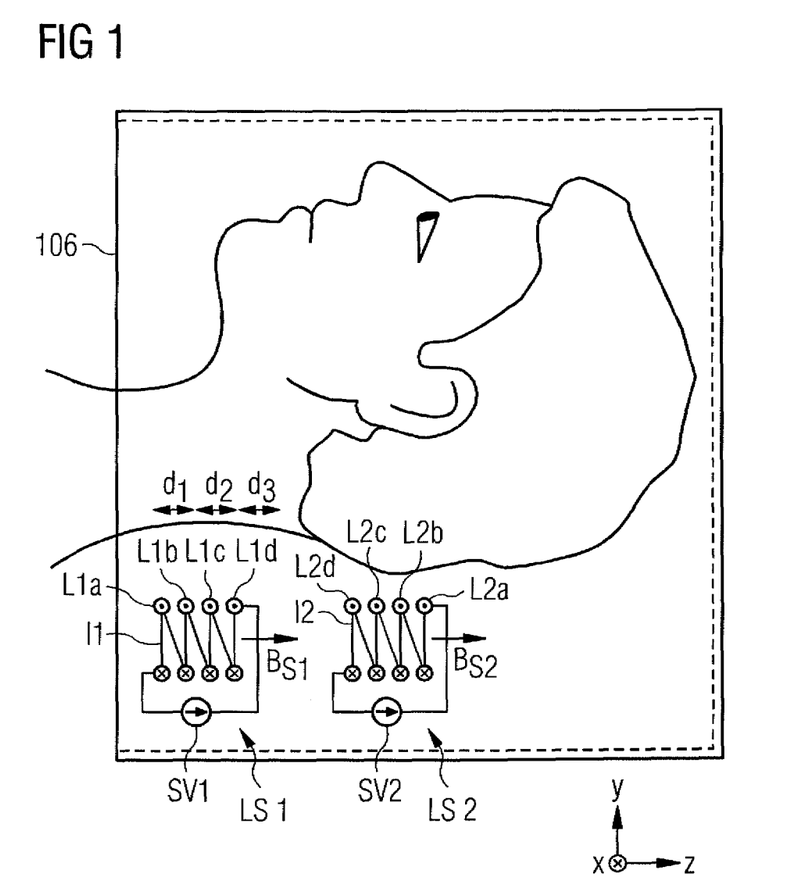
FIG. 1 shows a view of a patient and one embodiment of a head coil from one side in a longitudinal section.

FIG. 1 shows an exemplary embodiment of a local coil 106 (e.g., a nape of the neck-head local coil) that may be placed over a head K and nape of the neck N of a patient 105 like a helmet, for example.

The local coil 106 has a number of shim coils LS1, LS2 (e.g., two shim coils) each with a number of leads L1a, L1b, L1c, L1d or L2a, L2b, L2c, L2d, respectively, by which shim coils (e.g., if a current I1 or I2 is flowing through, and/or a voltage is applied from a current and/or voltage source or energy source SV1, SV2) a shim field BS1 or BS2 may be generated in each case in order to homogenize the magnetic field (e.g., $B_0$) in the area of the nape of the neck N of a patient 105 in order to improve the image quality.

The current and/or voltage source (or energy source) SV1 for the shim coil LS1 may be switched independently of the current and/or voltage source (or energy source) SV2 for the shim coil LS2 (e.g., in order to apply a current/voltage to the respective shim coil).

Current and/or voltage source (or energy source) SV1, SV2 are current and/or energy sources present, for example, in the local coil for other purposes.

Figure 2:
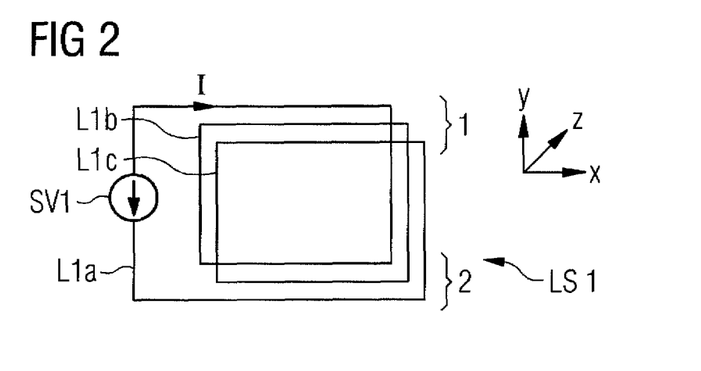
FIG. 2 shows a view from above of roughly rectangular leads of a shim coil of one embodiment of a local coil connected to one another, located behind one another in the z-direction.

In FIG. 2, in an exemplary embodiment of a local coil 106, a number of leads L1a, L1b, L1c, L1d of a shim coil LS1 are connected in series to one another and arranged behind one another in the z direction, so that the field effect of the leads L1a, L1b, L1c, L1d approximately adds and the leads L1a, L1b, L1c, L1d have an approximately rectangular cross section.

Figure 3:
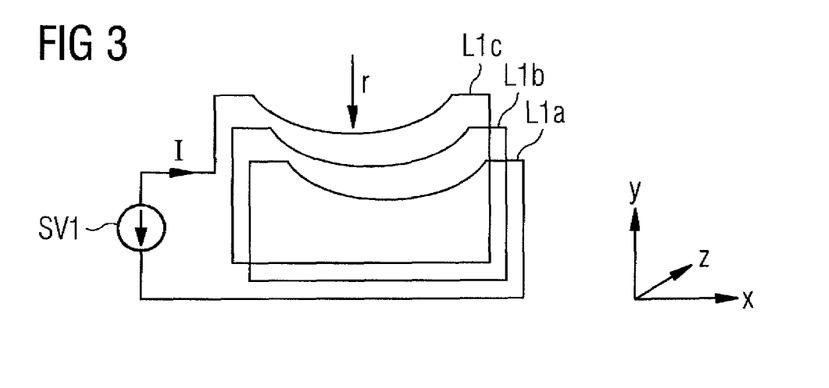
FIG. 3 shows a view from above of leads of a shim coil of one embodiment of a local coil located behind one another in the z-direction curved roughly at right angles on the neck.

In FIG. 3, in a further exemplary embodiment of a local coil 106, a number of leads L1a, L1b, L1e, L1d of a shim coil LS1 are connected in series to one another, disposed behind one another in the z-direction and have an approximately rectangular cross section with the exception of an ergonomic curve r in the area of the nape of the neck of a patient.

Figure 4:
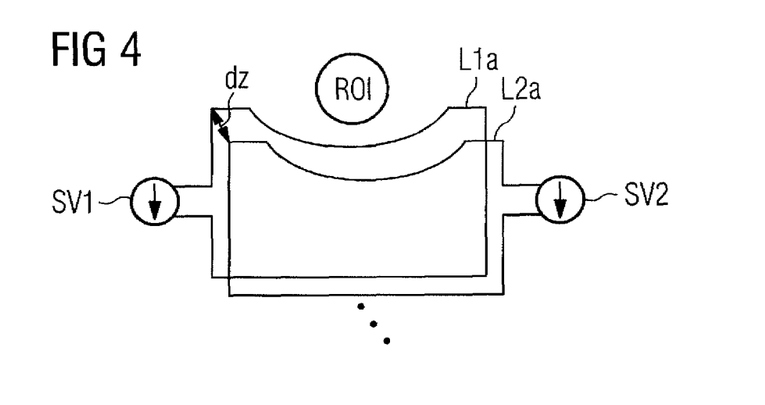
FIG. 4 shows a view from above of leads of two shim coils of one embodiment of a local coil able to be switched on independently of one another by voltage/current sources.

FIG. 4 shows a further exemplary embodiment of a local coil 106 below a nape of the neck area ROI of a patient to be recorded Two shim coils LS1, LS2 are connected by only one lead L1a or L2a in each case to a current and/or voltage source SV1 for the shim coil LS1 and the current and/or voltage source SV2 for the shim coil LS2.

Figure 5:
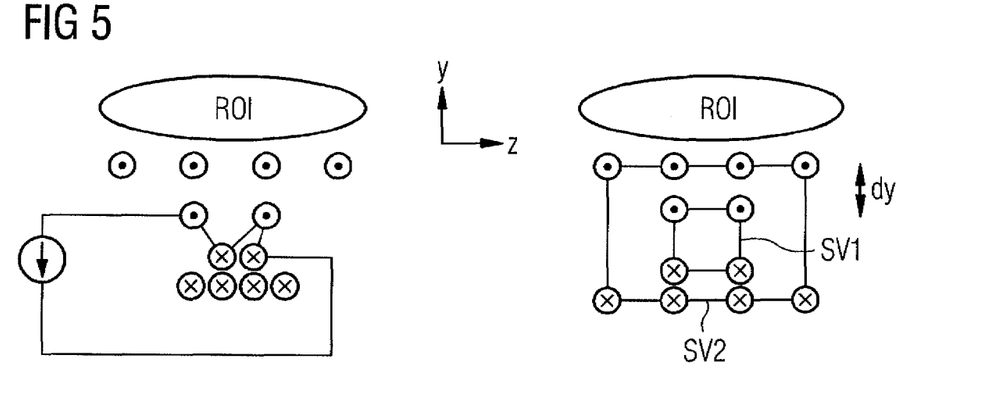
FIG. 5 shows, on the left, a side view and, on the right, a view from above of leads of two shim coils of one embodiment of a local coil able to be switched on independently of one another by voltage/power sources, one of the shim coils being located within the other of the shim coils.

FIG. 5, in longitudinal section on the left and a cross section on the right, shows a further exemplary embodiment of a local coil 106 below a nape of the neck area ROI of a patient to be recorded. One shim coil LS1 is located within the further shim coil LS2.

Figure 6:
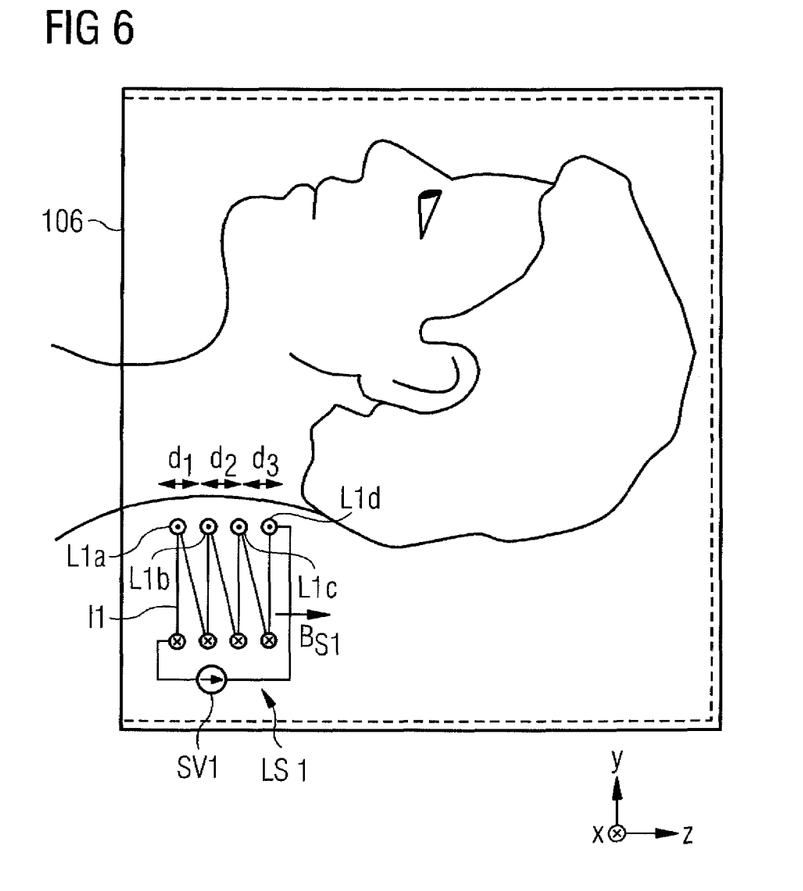
FIG. 6 shows exemplary distances of the leads of a shim coil from one another.

FIG. 6 shows an exemplary embodiment of a local coil 106 below a nape of the neck area of the patient. For illustrative purposes, only one shim coil LS1 of a number of coils is shown in order to show possible distances d1, d2, d3 of leads L1a, L1b, L1e, L1d (e.g., of the shim coil LS1) from one another. Distances d1, d2, d3 between leads L1a, L1b, L1e, L1d (e.g., of the shim coil LS1) may be the same or different.

Figure 7:
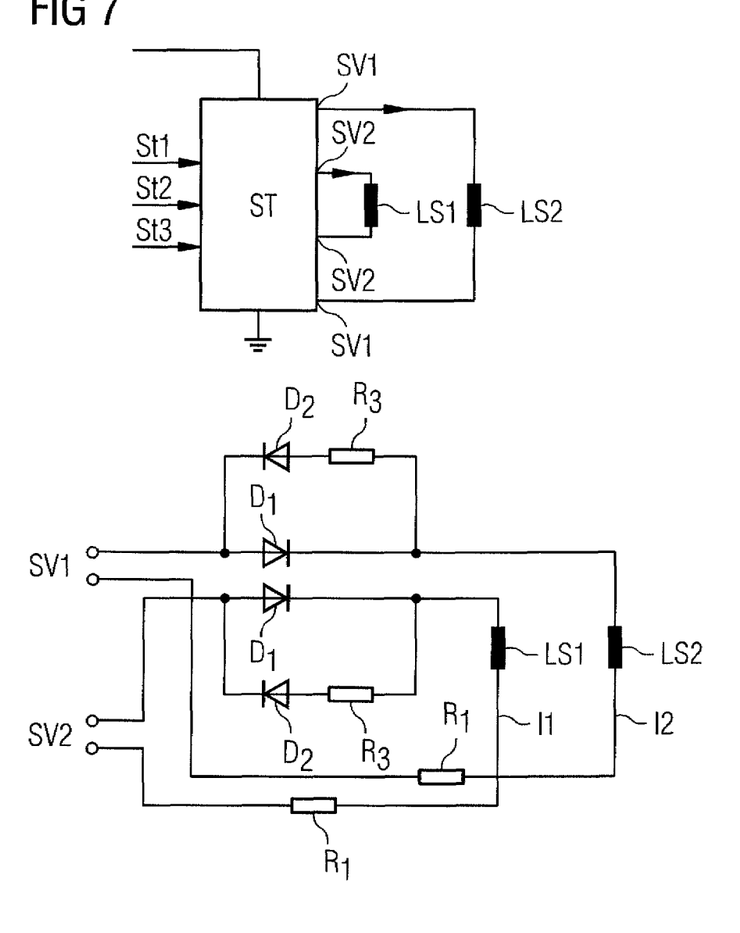
FIG. 7 shows a connection to voltage/current sources via diodes and resistors of two shim coils of one embodiment of a local coil able to be switched on independently of one another by voltage/current sources.

FIG. 7 shows a connection to voltage/current sources SV1, SV2 via diodes D1, D2 and resistors R1 of two shim coils LS1, LS2 of a local coil that may be switched independently of one another by voltage/power sources.

In the upper part of FIG. 7, control signals St1, St2, St3 from a controller 110 117 of an MRT control a controller ST of the local coil 106 so that the controller ST switches the corresponding current/voltage from a voltage/current source SV1 present in the local coil to one or more shim coils LS1 and/or LS2.

In the lower part of FIG. 7, a PIN diode channel 1 and a PIN diode channel 2 in a local coil are shown as examples of voltage sources/current sources, of which the current/voltage (e.g., the options available are 10 mA or 100 mA or 30V; three states are possible for the shim coil) may optionally be applied to the shim coils.

If, for example, in FIG. 7, the diode channel 1 (SV1) and/or the PIN diode channel 2 (SV2) each output 10 mA of current, the diodes D1 conduct, and a corresponding channel I1, I2 (e.g., at a first level) flows through shim coils LS1 and LS2.

If, for example, in FIG. 7, the diode channel 1 (SV1) and/or the PIN diode channel 2 (SV2) each output 100 mA of current, the diodes D1 conduct, and a corresponding current I1, I2 (e.g., at a second level) flows through shim coils LS1 and LS2.

If, for example, in FIG. 7, the diode channel 1 (SV1) and/or the PIN diode channel 2 (SV2) each output 30V, the diodes D2 conduct, and a corresponding current I1, I2 (e.g., at a third level) flows through shim coils LS1 and LS2.

A PIN diode channel 1=SV1 (e.g., like 2=SV2) may optionally output 10 mA or 100 mA or 30V (e.g., three possible currents I1, I2 and thereby states are possible for each shim coil LS1, LS2).

If at a PIN diode channel 1=SV1, optionally 10 mA or 100 mA or 30V may be output: for 30V with a generation of a current I1 in a shim coil LS1 in one direction and for 10 mA and/or 100 mA with the generation of a current I1, I2 in a shim coil LS1 in the opposite direction, by selecting 30V or 10 mA/100 mA output from SV1, the field direction of the shim field BS1 of the shim coil LS1 may be selected. The same applies for SV2 and LS2.

The field direction of the shim field BS1 that the shim coil LS1 generates and the field direction of the shim field BS2 that the shim coil LS2 generates may be selected as the same or opposing, and the shim fields may thus strengthen each other or mutually weaken each other.

The one PIN diode channel 1=SV1 (e.g., like 2=SV2) may optionally output 10 mA or 100 mA or 30V (e.g., three possible currents I1, I2 and thereby states are possible for each shim coil LS1, LS2).

The resistors R1 each limit the current I1, I2 through the shim coils at a desired level.

To decouple the shim coils from the gradient field of the MRT, an alignment of the coil axis of the shim coils in parallel to the x-axis may be advantageous.

Figure 8:
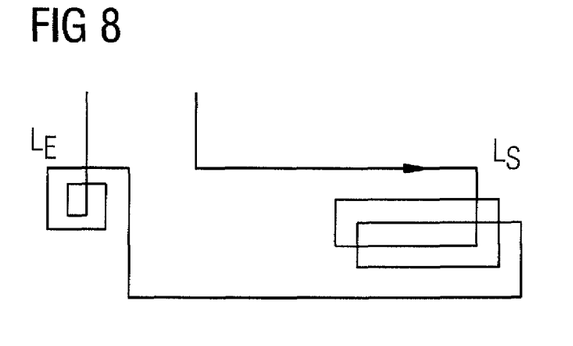
FIG. 8 shows an exemplary gradient system decoupling of a shim coil of one embodiment of a local coil with a decoupling coil.

FIG. 8 shows a gradient field decoupling of the shim coil LS1 of a local coil 106 with a decoupling coil LE that is connected in series antiparallel in relation to the shim coil LS1 (e.g., with an opposing winding direction).

The gradient field, which may induce a voltage US in the shim coil, may generate a voltage −US in the decoupling coil LE in the opposite direction. The generated voltage −US may compensate for the current through the gradient field induction to around zero, especially if the shim coil LSI and the decoupling coil LE are located in a sufficiently homogeneous gradient field.

The decoupling coil LE in local coil 106 is at a sufficient distance from the imaging volume ROI for the field of the decoupling coil LE not to act on the patient while generating artifacts in the imaging (e.g., also further away than the shim coil LS1).

Figure 9:
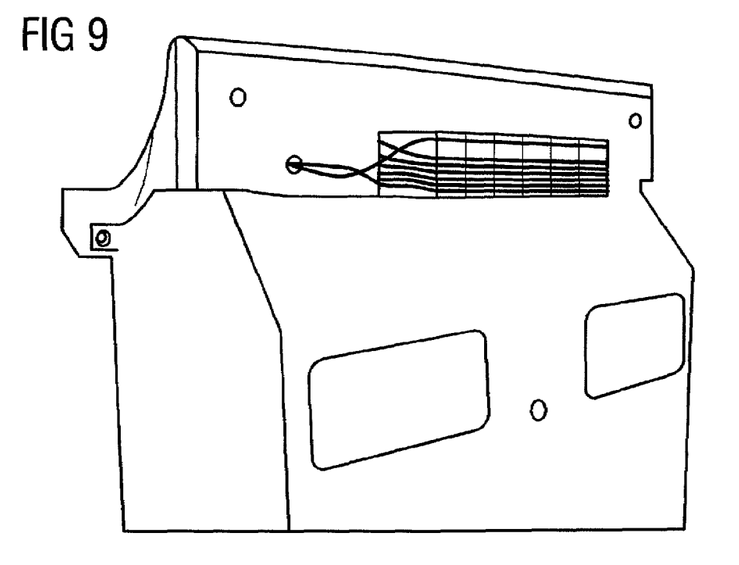
FIG. 9 shows a perspective diagram of one embodiment of a local coil with a shim coil.

FIG. 9 shows a perspective diagram of one embodiment of a local coil with the shim coil below a neck coil 106 with seven leads/windings and a size of 12*4.5 cm.

Figure 10:
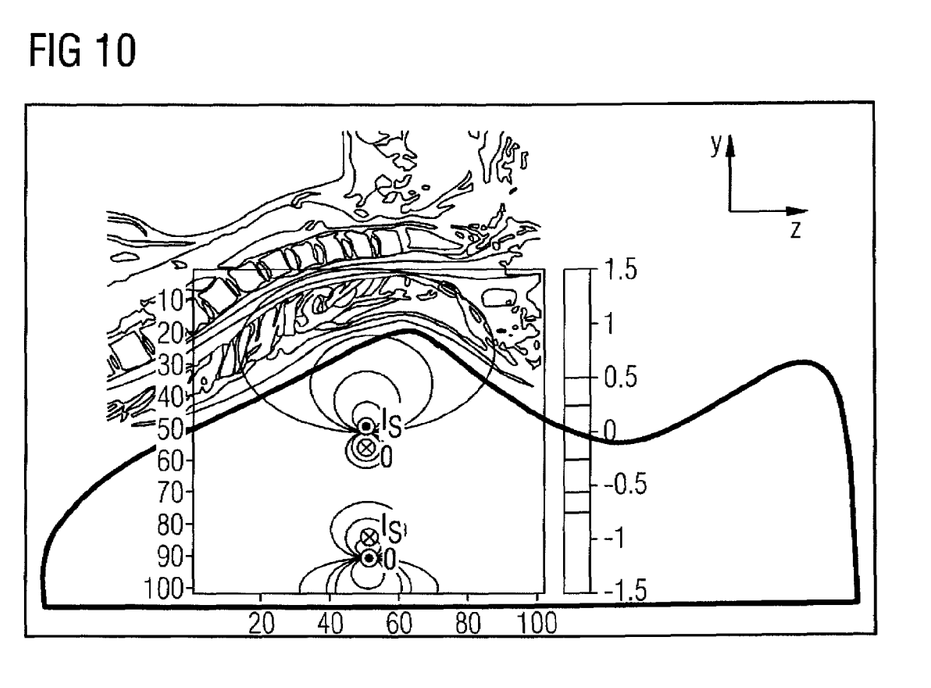
FIG. 10 shows an exemplary shim field curve in an area of one embodiment of a shimmed local coil.

FIG. 10 shows an exemplary shim field curve in the area of a shimmed local coil.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A local coil for an imaging system, the local coil comprising:
one or more coil elements; and
a plurality of shim coils,
wherein a current for generating a shim field in one shim coil of the plurality of shim coils is switchable on and switchable off,
wherein a current for generating a shim field in another shim coil of the plurality of shim coils is switchable on and switchable off,
wherein the currents for generating the shim fields are switchable on and switchable off independently of one another in the one shim coil and the other shim coil, and
wherein at least the one shim coil of the plurality of shim coils is located in the local coil at a position anterior, posterior, or anterior and posterior to a position for a head, a neck, or the head and the neck in the local coil, the one or more shim coils enclose the position for the head, the neck, or the head and the neck of a patient, or a combination thereof.

2. The local coil as claimed in claim 1, wherein the imaging system comprises a magnetic resonance tomography (MRT) device.

3. The local coil as claimed in claim 1, wherein one or more shim coils of the plurality of shim coils comprise leads, and wherein the leads are rectangular in cross-section.

4. The local coil as claimed in claim 1, wherein a shim coil of the plurality of shim coils comprises a plurality of rectangular-shaped leads, and
wherein the plurality of rectangular-shaped leads are connected in series to one another.

5. The local coil as claimed in claim 1, wherein one or more shims of the plurality of shims comprise leads that are at least approximately rectangular in cross-section, a side of the rectangular cross-section configured to rest against the patient, and
wherein the side is arched in shape, curves down into a shim coil interior, or a combination thereof.

6. The local coil as claimed in claim 1, wherein several shim coils of the plurality of shim coils are controllable independently of one another, current or voltage is applicable to the several shim coils for generating a current in the several shim coils, or a combination thereof.

7. The local coil as claimed in claim 1, wherein the one shim coil of the plurality of shim coils is located within the other shim coil of the plurality of shim coils.

8. The local coil as claimed in claim 1, wherein the one shim coil of the plurality of shim coils is spaced in relation to the other shim coil of the plurality of shim coils in the y direction, in the vertical direction, or the y direction and the vertical direction when used in the imaging system.

9. The local coil as claimed in claim 1, wherein the one shim coil of the plurality of shim coils comprises a plurality of leads, the plurality of leads being disposed behind one another viewed in a direction of introduction of a patient into the imaging system, a longitudinal direction of the patient, or the direction of introduction and the longitudinal direction.

10. The local coil as claimed in claim 1, wherein the one shim coil of the plurality of shim coils comprises a plurality of leads, the plurality of leads, for imaging, run at least in one area in an approximately horizontal direction.

11. The local coil as claimed in claim 1, wherein the one shim coil of the plurality of shim coils comprises at least three leads, the at least three leads, viewed in a direction of introduction of a patient into the imaging system, a longitudinal direction of the patient, or the direction of introduction and the longitudinal direction, being at a same distance from one another.

12. The local coil as claimed in claim 1, wherein the one shim coil of the plurality of shim coils comprises at least three leads, the at least three leads, viewed in a direction of introduction of a patient into the imaging system, a longitudinal direction of the patient, or the direction of introduction and the longitudinal direction, being at different distances from one another.

13. The local coil as claimed in claim 1, wherein the one shim coil of the plurality of shim coils comprises a plurality of leads, the plurality of leads, viewed in a direction of introduction of a patient into the imaging system, a longitudinal direction of the patient, or the direction of introduction and the longitudinal direction, forming windings of the shim coil connected one behind the other.

14. The local coil as claimed in claim 1, wherein the shim field in the one shim coil and the shim field in the other shim coil overlay each other in a switched-on state.

15. The local coil as claimed in claim 14, wherein the shim field in the one shim coil and the shim field in the other shim coil overlay each other constructively or destructively in the switched-on state.

16. The local coil as claimed in claim 1, wherein the local coil comprises a head coil, a head-neck coil, a nape of the neck coil, a back coil, an abdomen coil, a shoulder coil, a back coil, a joint coil, or a chest coil.

17. The local coil as claimed in claim 1, wherein at least the one shim coil and the other shim coil each have a spatial distance between shim coil leads of the shim coils that allows a strength of the shim field and a structure of the shim field to be varied, the spatial distance being at least 0.5 cm, 1 cm, 2 cm, 3 cm, 4 cm, or 5 cm.

18. The local coil as claimed in claim 1, wherein at least the one shim coil and the other shim coil each have a spatial distance between shim coil leads of the shim coil that is at least 0.5 cm, 1 cm, 2 cm, 3 cm, 4 cm, or 5 cm.

19. The local coil as claimed in claim 1, wherein the plurality of shim coils is connected to one or more coil interfaces also present for purposes other than for the plurality of shim coils in the local coil.

20. The local coil as claimed in claim 1, wherein the plurality of shim coils is connected to a supply voltage source for coil electronics, a supply voltage source for switchover signals for PIN diodes in the local coil, or a combination thereof.

21. The local coil as claimed in claim 1, further comprising at least one connection with at least two voltage sources.

22. The local coil as claimed in claim 21, wherein the at least two voltage sources comprise one source of a negative voltage, one source of a positive voltage, one source of a current, another source of a current, or any combination thereof.

23. The local coil as claimed in claim 1, further comprising at least one connection with at least two states, the at least two states being controllable by control signals for setting different shim states of the plurality of shim coils by output of corresponding voltages, currents, or voltages and currents to the plurality of shim coils.

24. The local coil as claimed in claim 1, wherein all or individual shim coils of the plurality of shim coils only have shim voltage, shim current, or shim voltage and shim current applied during a specific period of time.

25. The local coil as claimed in claim 24, wherein the local coil is a head coil, and wherein the specific period of time is a transmit phase of the head coil.

26. The local coil as claimed in claim 1, wherein the local coil is configured so that shim voltages, shim currents, or shim voltages and shim currents are only applied in the local coil during a saturation pulse to the plurality of shim coils.

27. The local coil as claimed in claim 1, further comprising a circuit,
wherein one or more shim voltages present in the circuit, one or more shim currents present in the circuit, or the one or more shim voltages and the one or more shim currents are switchable independently to at least two shim coils of the plurality of shim coils, so that a number of shim states switchable in the local coil is the product of the sum of the possible shim voltages plus shim currents with a number of shim coils switchable independently of one another.

28. The local coil as claimed in claim 1, wherein a coil axis of one or more shim coils of the plurality of shim coils is approximately parallel to the z axis.

29. The local coil as claimed in claim 1, further comprising decoupling coils operable to decouple the plurality of shim coils from the imaging system or the local coil.

30. The local coil as claimed in claim 29, wherein the decoupling coils comprise between one and three coils for each spatial direction orthogonal to one another, with a winding orientation in antiparallel opposition to a winding orientation of the plurality of shim coils.

31. The local coil as claimed in claim 1, further comprising a series connection of resistors operable to reduce a gradient-induced current, the resistors being rated at 5-500 Ohm.

32. The local coil as claimed in claim 1, wherein the local coil is placeable on the head, the neck, or the head and the neck of a patient.

33. The local coil as claimed in claim 1, wherein at least the one shim coil of the plurality of shim coils is disposed in a housing of the local coil.

34. The local coil as claimed in claim 1, wherein at least one switchable current supply, at least one voltage supply, a controller, or a combination thereof is disposed in a housing of the local coil.

35. The local coil as claimed in claim 1, further comprising a controller of shim current or of shim voltage for the plurality of shim coils, the controller being disposed in the local coil, the imaging system, or the local coil and the imaging system.

36. The local coil as claimed in claim 1, wherein the plurality of shim coils is operable to be switched on simultaneously, alternatively to one another, or simultaneously and alternatively to one another by switching on or switching off the currents in the plurality of shim coils, voltage to the plurality of shim coils, or a combination thereof.

37. The local coil as claimed in claim 1, further comprising a power supply of the plurality of shim coils, a voltage source, a current source, or the voltage source and the current source of the power supply being controllable.

38. The local coil as claimed in claim 1, wherein the plurality of shim coils is mechanically rigidly connected to a housing of the local coil.

39. The local coil as claimed in claim 1, wherein a lead of the one shim coils of the plurality of shim coils is arranged in an area of the local coil for adapting a shape of the local to the nape of the neck of a patient.

40. The local coil as claimed in claim 1, wherein the plurality of shim coils are switchable on independently of one another by application of a current, a voltage, or the current and the voltage of a source for generating a shim field in a switched-on state, and
wherein the plurality of shim coils are each switchable off independently of one another in a switched-off state by applying a current, a voltage, or the current and the voltage with a current of a source generating a shim field.

41. A local coil for an imaging system, the local coil comprising:
a plurality of shim coils,
wherein a current for generating a shim field in one shim coil of the plurality of shim coils is switchable on and switchable off,
wherein a current for generating a shim field in another shim coil of the plurality of shim coils is switchable on and switchable off,
wherein the currents for generating the shim fields are switchable on and switchable off independently of one another in the one shim coil and the other shim coil, and
wherein the plurality of shim coils is connected to a supply voltage source for coil electronics, a supply voltage source for switchover signals for PIN diodes in the local coil, or a combination thereof.

42. A local coil for an imaging system, the local coil comprising:
a plurality of shim coils; and
decoupling coils operable to decouple the plurality of shim coils from the imaging system or the local coil,
wherein the decoupling coils comprise between one and three coils for each spatial direction orthogonal to one another, with a winding orientation in antiparallel opposition to a winding orientation of the plurality of shim coils,
wherein a current for generating a shim field in one shim coil of the plurality of shim coils is switchable on and switchable off,
wherein a current for generating a shim field in another shim coil of the plurality of shim coils is switchable on and switchable off, and
wherein the currents for generating the shim fields are switchable on and switchable off independently of one another in the one shim coil and the other shim coil.

* * * * *